United States Patent [19]

Cohen

[11] Patent Number: 5,756,782
[45] Date of Patent: May 26, 1998

[54] METHOD FOR PURIFYING DIACETYLRHEIN

[75] Inventor: Avraham Cohen, Tel Aviv, Israel

[73] Assignee: Steba Beheer B.V., The Hague, Netherlands

[21] Appl. No.: 722,127

[22] PCT Filed: Feb. 7, 1996

[86] PCT No.: PCT/IB96/00093

§ 371 Date: Mar. 18, 1997

§ 102(e) Date: Mar. 18, 1997

[87] PCT Pub. No.: WO96/24572

PCT Pub. Date: Aug. 15, 1996

[30] Foreign Application Priority Data

Feb. 7, 1995 [CH] Switzerland ................ 342/95

[51] Int. Cl.$^6$ ............................................. C07C 67/60
[52] U.S. Cl. ........................................................ 552/262
[58] Field of Search ............................ 552/262; 514/548

[56] References Cited

U.S. PATENT DOCUMENTS

| | | | |
|---|---|---|---|
| 4,244,968 | 1/1981 | Friedmann | 514/548 |
| 4,346,103 | 8/1982 | Friedmann | 514/548 |
| 4,950,687 | 8/1990 | Dall'Asta et al. | 514/548 |
| 5,391,775 | 2/1995 | Carcasona et al. | 552/262 |
| 5,393,898 | 2/1995 | Carcasona et al. | 552/262 |

FOREIGN PATENT DOCUMENTS

| | | |
|---|---|---|
| 243968 | 11/1987 | European Pat. Off. . |
| 636602 | 2/1995 | European Pat. Off. . |
| 2711493 | 10/1977 | Germany . |
| 4120989 | 1/1993 | Germany . |
| 4120990 | 1/1993 | Germany . |

*Primary Examiner*—Richard L. Raymond
*Attorney, Agent, or Firm*—Clifford W. Browning; Woodard, Emhardt, Naughton Moriarty & McNett

[57] ABSTRACT

The present invention discloses a method for preparing purified diacetylrhein to be used in the preparation of drugs which includes the steps of:
(a) suspending a diacetylrhein containing various impurities and, in particular, relatively high amounts of aloe-emodin derivatives, in a mixture of organic solvent/water;
(b) adding a tertiary amine;
(c) adding to the solution obtained a salt of an acid and of an alkali metal or of an alkaline-earth metal;
(d) carrying out a hydrolysis in a weakly acidic medium;
(e) collecting the purified diacetylrhein, by filtration.

11 Claims, No Drawings

METHOD FOR PURIFYING DIACETYLRHEIN

This application is a 371 of PCT/IB96/00093, filed Feb. 7, 1995.

The present invention is concerned with a new purification method for diacetylrhein and, more particularly, a method which makes it possible to obtain diacetylrhein having a sufficient degree of purity to allow its use in the preparation of drugs.

BACKGROUND OF THE INVENTION

Arthrosis is a disease which is widely spread throughout the world, affecting more particularly elderly people, and manifesting itself by a degradation of the cartilaginous tissues, in particular of articulations and vertebrae, causing pain and having invalidating effects on the persons affected. The aging of the population in the western countries makes all the more necessary treatments capable of relieving pain in people suffering from this disease.

The administration of nonsteroidal anti-inflammatory and analgesic drugs, for example indomethacin, naproxen and aspirin generally makes it possible to relieve temporarily the patient, but has no real curative effect. More recently, it has been shown that certain derivatives of anthraquinone carboxylic acid and more particularly, of diacetylrhein produce good results in the treatment of certain forms of arthritis and arthrosis. Thus, it has been found that diacetylrhein, administered orally, has an anti-inflammatory and analgesic activity, and is effective for the treatment of arthrosis, without exhibiting any harmful secondary effect.

Derivatives of 1,8-dihydroxy-anthraquinone-3-carboxylic acid, including diacetylrhein, are described in the French patent FR-A-2 508 798.

Patent EP-A-243 968 describes alkaline salts of diacetylrhein, such as the sodium and potassium salts, obtained by the dissolution of diacetylrhein in a mixture of acetone and water, addition of triethylamine and conversion into a salt by a weak organic acid in an alcoholic medium (isobutanol). These sodium and potassium salts are used for making solutions designed for intravenous, intramuscular or intraperitoneal administration.

Diacetylrhein is a substance of vegetal origin, obtained from extraction products from aloe or from senna leaves. Thus, for example, it can be prepared by acetylation of 1,8-dihydroxy-anthraquinone-3-carboxylic acid (rhein), which can be obtained from the sennosides extracted from senna leaves. However, the diacetylrhein thus obtained contains important amounts of aloe-emodin, an undesirable secondary product which arises from the raw materials and its purification is difficult. It is also known how to prepare diacetylrhein by acetylation of barbaloin, followed by an oxidation with chromium oxide, but this technique also produces a final product having a high aloe-emodin content and is accompanied by the formation of chromic residues which as wastes, are difficult to eliminate by usual techniques.

Patents DE-A-4 120 989 and DE-A-120 990 describe methods for preparing diacetylrhein from sennosides which can contain aloe-emodin, including several steps consisting in oxidizing rhein-9-anthrone-8-glucosides, in separating the glucose residue and acetylating, the method further including a step of liquid-liquid separation. Although the purity of the diacetylrhein obtained is improved, the level of aloe-emodin in the product obtained remains relatively important (close to 20 ppm), which can result in the need to carry out additional purifications, lengthy and expensive.

SUMMARY OF THE INVENTION

The object of the present invention is a method for preparing a diacetylrhein of a very high purity, with a good yield.

Another object of the invention is a method for purifying diacetylrhein from a composition containing various impurities and in particular aloe-emodin derivatives, for obtaining a diacetylrhein free of aloe-emodin.

The invention extends finally to the diacetylrhein which is pure and substantially free of aloe-emodin thus obtained, to its use in the preparation of a drug for the treatment of arthrosis.

The diacetylrhein obtained by the method according to the present invention is of a purity such that it is substantially free of aloe-emodin, the actual level of aloe-emodin in the final product not being detectable by known techniques.

DETAILED DESCRIPTION OF THE PREFERRED EMBODIMENTS

The starting product used in the method of the invention is a diacetylrhein containing various impurities and, in particular, relatively high amounts of aloe-emodin derivatives, for example more than 50 ppm and in certain cases, amounts of aloe-emodin derivatives which can be in the order of 150 to 200 ppm. The expression "aloe-emodin derivatives" means not only aloe-emodin properly said, but also derivatives such as triacetyl-aloe-emodin.

The purification method for the diacetylrhein in accordance with the present invention consists in preparing a soluble salt of diacetylrhein, and then in carrying out a hydrolysis in a weakly acidic medium, to cause a precipitation. It includes substantially the steps consisting in:

(a) suspending the diacetylrhein in a mixture of organic solvent/water;
(b) adding a tertiary amine;
(c) adding to the solution obtained an acid salt of an alkali metal or of an alkaline-earth metal;
(d) carrying out a hydrolysis in a weakly acidic medium;
(e) collecting the purified diacetylrhein, by filtration.

By using the method in accordance with the present invention, one obtains a diacetylrhein of an excellent purity with a yield in excess of 90%, and which can reach 93 to 95% by selecting the operating conditions in an appropriate manner, as indicated hereafter. This yield can easily be risen to approximately 96% by recycling the filtration products.

On the other hand, the purity of the diacetylrhein thus obtained is remarkable, since the level of aloe-emodin and of derivatives of aloe-emodin arising from the raw materials is not detectable, the detection threshold of the analytical apparatuses conventionally used, such as HPLC apparatuses, being in the order of one ppm. Thus, the diacetylrhein purified obtained by the method of the present invention is substantially free of aloe-emodin. This result is particularly advantageous by comparison with the levels usually reported in methods known in the art, which are generally well in excess of 20 ppm.

The diacetylrhein in step (a) is suspended in a mixture of an organic solvent/water in a weight ratio comprised between 10/1 and 50/1 and preferably between 20/1 and 30/1. In accordance with the method of the invention, a minimal amount of water is used. The absence of water is unfavourable for the purification, whereas the use of an amount of water in excess to the values indicated above would have for consequence a decrease in the yield.

The organic solvent can be selected from acetone, methylethylketone, ethanol and dimethylacetamide.

The tertiary amine used in step (b) is preferably triethylamine and, more particularly, triethylamine in mixture with acetone, in a molar ratio lower than 1, preferably comprised between 0.3 and 0.6. On the other hand, the molar ratio of the tertiary amine to the diacetylrhein is preferably comprised between 1 and 1.2. A greater excess of amine improves neither the yield, nor the purity of the product obtained. By proceeding as indicated above, in accordance with the present invention, one achieves a complete dissolution of the amine salt, which makes it possible to substantially improve the industrial yield.

The salt used in step (c) is selected from sodium or potassium acetate, ethyl-hexanoate or propionate. One uses preferably an excess of potassium acetate, the molar ratio acetate/diacetylrhein being preferably in excess of 1.2 and more preferably comprised between 1.5 and 2.

The hydrolysis step is carried out preferably at a pH comprised between 3 and 5, by means of hydrochloric or sulphuric acid, by operating at a temperature comprised between 2° and 15° C. and more preferably between 5° and 8° C. A higher pH, in excess of 5, should be avoided, since it causes a degradation to monoacetylated products.

The method in accordance with the present invention is hence particularly advantageous, since it can be used for preparing industrially diacetylrhein of a pharmaceutical quality.

The purified diacetylrhein thus obtained is in the form of crystals which can be used directly in usual methods of manufacturing of pharmaceutical dosage forms, for example for the manufacture of capsules for oral administration.

The efficiency of the purified diacetylrhein obtained by the method of the invention was verified on usual experimental models. The results of toxicity trials ($DL_{50}$ after oral administration to rats and mice) are in agreement with those described in the literature. Clinical trials confirmed the efficiency of the pharmaceutical compositions, for oral administration, containing the diacetylrhein thus purified, more particularly in the treatment of arthrosis.

The following examples illustrate the invention without limiting the scope thereof.

EXAMPLE 1

In a mixture of acetone and deionized water (540 l of acetone, 25 l of water), there are suspended 50 kg of diacetylrhein containing impurities and more particularly aloe-emodin and triacetyl-aloe-emodin (level in excess of 150 ppm).

The suspension is kept under stirring at room temperature during 10 to 15 minutes and, after homogenization, is warmed to a temperature of 40°–45° C.

Thereafter, a mixture of triethylamine and acetone (15 kg of triethylamine for 19 kg of acetone) is added and is stirred continuously during approximately 10 minutes, until full dissolution of the ammonium salt of the diacetylrhein formed. The solution is then filtered to eliminate any trace of solid impurities.

25 kg of potassium acetate are added in the form of a powder, and the temperature of the reaction medium is reduced to 10° C and stirred continuously during approximately 1 hour.

The potassium salt of diacetylrhein thus formed is collected by filtration and washed with 150 l of acetone. Then the salt is dissolved in 2000 l of deionized water and 33% sulphuric acid is added until a pH of 5 is reached, and then the pH is reduced slowly to pH 4.

After cooling to approximately 10° C., the diacetylrhein formed by hydrolysis is collected by filtration, washed with deionized water until the pH is neutral and the product is then dried in an oven at about 60°–80° C. in such a manner as to achieve a moisture content lesser than 1%.

The yield in purified diacetylrhein is of 93%.

The filtrates from the diacetylrhein salt are acidified, concentrated to remove the acetone, taken up in 150 l of deionized water, and cooled to 10° C. to recover the crude diacetylrhein which is purified as indicated above. The overall yield of the purification is then increased to 96%.

The aloe-emodin content in the final purified product is assessed by chromatography (extraction method: the aloe-emodin, together with that obtained from the transformation of the triacetyl-aloe-emodin in the basic medium, is extracted from the diacetylrhein to be analyzed; the extract is then analyzed by HPLC on a C 18 column, at 254 nm). The result is lower than the detection threshold, which is of the order of one ppm.

EXAMPLE 2

One proceeds as in example 1, using as the starting material a crude diacetylrhein containing about 60 ppm of aloe-emodin, but replacing the potassium acetate by potassium propionate, prepared from the corresponding acid in an aqueous solution.

The yield, before recycling the filtrates, is of 85%.

The content of aloe-emodin in the purified product remains lower than the detection threshold by the HPLC apparatus.

EXAMPLE 3

One proceeds as in the example 1, but using for the hydrolysis of the ammonium salt, hydrochloric acid instead of sulphuric acid, and replacing the solvent mixture acetone/deionized water by a mixture ethanol/water.

One obtains results equivalent to those indicated above.

EXAMPLE 4

One proceeds as indicated in example 1 above, but using an amount of water double of that in example 1 for the preparation of the suspension of diacetylrhein (50 l instead of 25 l).

One then finds that the yield is slightly lower (80% at the first step, which can be improved by recycling), but the purity is not modified (content lower than the detection threshold).

I claim:

1. A method for purifying diacetylrhein comprising the steps of:

(a) suspending the diacetylrhein in a mixture of organic solvent/water;

(b) adding a tertiary amine;

(c) adding to the solution obtained, a salt of an acid and of an alkali metal or of an alkaline-earth metal;

(d) carrying out a hydrolysis in a weakly acidic medium;

(e) collecting the purified diacetylrhein, by filtration.

2. A method according to claim 1, wherein said hydrolysis is carried out at a pH comprised between 3 and 5.

3. A method according to claim 1, wherein said hydrolysis is carried out by means of hydrochloric acid or sulphuric acid.

4. A method according to claim 1, wherein said hydrolysis is carried out at a temperature comprised between 2° C. and 15° C.

5. A method according to claim 4, wherein said temperature is comprised between 5° C. and 8° C.

6. A method according to claim 1, wherein said diacetylrhein in step (a) is suspended in a mixture of organic solvent/water in a weight ratio comprised between 10/1 and 50/1.

7. A method according to claim 6, wherein said organic solvent is selected from acetone, methylethylketone, ethanol and dimethylacetamide.

8. A method according to claim 1, wherein said tertiary amine used in step (b) is triethylamine.

9. A method according to claim 8, wherein said triethylamine is used in a mixture with acetone in a molar ratio triethylamine/acetone comprised between 0.3 and 0.6.

10. A method according to claim 1, wherein said salt used in step (c) is selected from sodium or potassium acetate, ethylhexanoate and propionate.

11. A method according to claim 1 wherein said hydrolysis of step (d) is carried out in a sulphuric acid or a hydrochloric acid medium with a solvent mixture acetone/water or ethanol/water.

* * * * *